(12) United States Patent
Lutze et al.

(10) Patent No.: US 11,629,109 B2
(45) Date of Patent: Apr. 18, 2023

(54) EXTRACTIVE DISTILLATION COLUMN SYSTEM AND THE USE THEREOF IN THE SEPARATION OF BUTENES FROM C4-HYDROCARBON STREAMS

(71) Applicant: Evonik Operations GmbH, Essen (DE)

(72) Inventors: Philip Lutze, Dinslaken (DE); Stephan Peitz, Oer-Erkenschwick (DE); Armin Matthias Rix, Marl (DE); Tanita Valèrie Six, Dortmund (DE); Moritz Schröder, Muenster (DE); Niklas Paul, Marl (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 17/808,250

(22) Filed: Jun. 22, 2022

(65) Prior Publication Data

US 2022/0411352 A1 Dec. 29, 2022

(30) Foreign Application Priority Data

Jun. 25, 2021 (EP) .................................... 21181624

(51) Int. Cl.
| | | |
|---|---|---|
| *C07C 7/08* | (2006.01) | |
| *B01D 3/40* | (2006.01) | |
| *B01D 3/14* | (2006.01) | |
| *B01D 3/00* | (2006.01) | |

(52) U.S. Cl.
CPC ................ *C07C 7/08* (2013.01); *B01D 3/007* (2013.01); *B01D 3/148* (2013.01); *B01D 3/40* (2013.01)

(58) Field of Classification Search
CPC .... C07C 7/04; C07C 7/05; C07C 7/06; C07C 7/08; C07C 9/10; C07C 9/12; C07C 11/08; C07C 11/09; C07C 11/16; C07C 11/167; B01D 3/141; B01D 3/143; B01D 3/148

See application file for complete search history.

(56) References Cited

U.S. PATENT DOCUMENTS

| | | | |
|---|---|---|---|
| 6,514,387 B1 | 2/2003 | Emmrich et al. | |
| 7,556,717 B2 * | 7/2009 | Heida | ........................ C07C 7/08 203/99 |
| 2005/0199482 A1 * | 9/2005 | Heida | ...................... B01D 3/40 203/99 |
| 2006/0021911 A1 | 2/2006 | Adrian et al. | |
| 2006/0241329 A1 | 10/2006 | Heida | |
| 2007/0039813 A1 | 2/2007 | Heida | |
| 2014/0124358 A1 | 5/2014 | Schwint et al. | |

FOREIGN PATENT DOCUMENTS

| | | |
|---|---|---|
| DE | 2359300 | 6/1974 |
| DE | 19849651 | 5/2000 |
| WO | 2004/011406 | 2/2004 |
| WO | 2004/103937 | 12/2004 |
| WO | 2005/009931 | 2/2005 |

OTHER PUBLICATIONS

European Search Report dated Dec. 21, 2021, in European Application No. 21181624.4, 10 pages

* cited by examiner

*Primary Examiner* — Jonathan Luke Pilcher
(74) *Attorney, Agent, or Firm* — Grüneberg and Myers, PLLC (57) ABSTRACT

An extractive distillation column system contains a combination column and a side rectification column. A process can be used for separation of butenes from C4-hydrocarbon streams using the extractive distillation column system.

18 Claims, 5 Drawing Sheets

EXTRACTIVE DISTILLATION COLUMN SYSTEM AND THE USE THEREOF IN THE SEPARATION OF BUTENES FROM C4-HYDROCARBON STREAMS

CROSS-REFERENCE TO RELATED APPLICATIONS

This application claims priority to European Application No. 21181624.4, filed on Jun. 25, 2021, the content of which is hereby incorporated by reference in its entirety.

BACKGROUND OF THE INVENTION

Field of the Invention

The present invention relates to an extractive distillation column system which comprises a combination column (1) and a side rectification column (2). The present invention further relates to a process for separation of butenes from C4-hydrocarbon streams using the extractive distillation column system.

Description of Related Art

The separation of butenes from C4-hydrocarbon streams containing butanes in addition to the butenes is a known process. This typically employs the extractive distillation, wherein an aprotic solvent (for example N-methyl-2-pyrrolidone (NMP) or acetonitrile (ACN)) is used to increase the relative volatility of the alkanes compared to the alkenes. Plants for performing a corresponding extractive distillation typically comprise two separate columns. In one column, the absorber, the butenes are dissolved in the solvent and the butanes separated as tops product. The solvent laden with the butenes is subsequently freed of the butenes in a stripping column, the desorber, at elevated temperature and/or reduced pressure, and said butenes are obtained in enriched form at the top of the desorber. The solvent freed of the butenes is then recycled to the absorber.

In the known plants having (spatially) separate absorber and desorber columns a liquid stream is passed from the absorber to the desorber. This is typically achieved using a pump. Such a pump is costly to acquire and ultimately also leads to significant operating and maintenance costs. Corresponding plants also require sufficient space for the respective columns and other assemblies. However, sufficient space is not always available. There is therefore a need for building and operating plants for separation of butenes from C4-hydrocarbon streams in a manner that is more cost- and space-efficient.

SUMMARY OF THE INVENTION

It was accordingly the object of the present invention to provide an extractive distillation column system which requires less space and is less costly to operate. Further, it was the object to provide a process for separation of butenes which is space- and cost-efficient.

These objects are achievable by the embodiment of the extractive distillation column system proposed in the description below and the process described below. Preferred embodiments are also specified in the description below.

The invention also includes the following embodiments:
1. Extractive distillation column system for separation of butenes from a C4-hydrocarbon stream which contains at least butenes and butanes using a solvent, wherein the extractive distillation column system comprises a combination column (1) and a side rectification column (2),
   wherein the combination column (1) viewed from top to bottom comprises at least the following different sections: a top section in which a stream enriched in butanes compared to the employed C4-hydrocarbon stream is obtained; a random packing section which comprises at least two random packing beds; a collection section which comprises at least two liquid collectors, preferably chimney trays: a regeneration section which comprises at least one random packing bed; and a bottom section in which the solvent is obtained: and wherein arranged on the combination column (1) are at least two side evaporator systems (5, 6) in which in each case a liquid phase from one of the liquid collectors of the collection section is at least partially evaporated and subsequently recycled via a respective inlet (5a, 6a) to the collection section, wherein the inlet (5a) is arranged spatially at least one liquid collector above the inlet (6a);
   wherein the side rectification column (2) comprises at least two separating trays or at least one random packing or structured packing bed and is supplied with a gaseous phase which is obtained from the collection section of the combination column (1) below the inlet (5a) but above or at the same height as the inlet (6a).
2. Extractive distillation column system according to embodiment 1, wherein the extractive column system comprises a feed evaporator (4) which at least partially evaporates the C4-hydrocarbon stream before it is passed into the combination column (1).
3. Extractive distillation column system according to embodiment 2, wherein the solvent obtained in the bottom of the combination column (1) is recycled to the inlet for the solvent.
4. Extractive distillation column system according to embodiment 3, wherein the solvent is used for heat integration where heat of the solvent is transferred in the first side evaporator system (5), in the second side evaporator system (6) and in the feed evaporator (4).
5. Extractive distillation column system according to any of the preceding embodiments, wherein arranged at the bottom section of the combination column (1) is a bottoms evaporator (7) which at least partially evaporates the liquid obtained in the column bottom to outgas any residues of butenes from the solvent.
6. Extractive distillation column system according to any of the preceding embodiments, wherein a stream enriched in butenes is withdrawn at the top of the side rectification column (2),
7. Process for separation of butenes from a C4-hydrocarbon stream containing at least butenes and butanes by extractive distillation in an extractive distillation column system according to any of embodiments 1 to 6, wherein the separation of the butenes is effected by the following steps:
   supplying a C4-hydrocarbon stream at least partially evaporated in a feed evaporator (4) to the random packing section of the combination column (1) and supplying the liquid solvent at least one random packing bed above the C4-hydrocarbon stream, with the result that the C4-hydrocarbon stream and the solvent are brought into contact with one another and predominantly butenes are transferred from the C4-hydrocarbon stream to the solvent to obtain a laden solvent;

wherein the laden solvent is collected in a liquid collector of the collection section, passed through a first side evaporator system (5), at least partially evaporated therein and then recycled to the collection section via the inlet (5a);

wherein a liquid phase obtained in a further liquid collector of the collection section is passed through a second side evaporator system (6), at least partially evaporated therein and then via the inlet (6a) recycled to the collection section, from where the liquid phase passes into the regeneration section;

wherein the liquid phase obtained below the last random packing bed of the regeneration section and containing the solvent and residual butenes and/or butanes is passed through a bottoms evaporator (7) and then passed into the bottom section, with the result that any butenes and/or butanes present in the solvent are at least partially outgassed and the resulting solvent is withdrawn as a bottoms stream and recycled to the random packing section; and providing a gaseous stream containing at least butenes and residual solvent below the inlet (5a) but above or at the same height as the inlet (6a) from the collection section and supplying this gaseous stream to the side rectification column (2), with the result that a stream enriched in butenes is obtained at the top of the side rectification column, characterized in that the heat of the solvent withdrawn as the bottoms stream is at least partially used for heat integration where heat of the solvent is transferred in the first side evaporator system (5), in the second side evaporator system (6) and in the feed evaporator (4).

8. Process according to embodiment 7, wherein the employed solvent is NMP.
9. Process according to embodiment 7 or 8, wherein the heat for evaporation in the bottoms evaporator (7) is introduced in a heat exchanger by heat transfer with a suitable heat transfer medium, in particular heating steam,
10. Process according to embodiment 9, wherein the employed heating steam undergoes at least partial condensation in the heat exchanger, thus generating a hot condensate at a pressure of 10 to 20 bar absolute, preferably 12 to 17 bar absolute, and a temperature of 150° C. to 210° C., preferably 160° C. to 200° C., which is passed to a condensate container.
11. Process according to embodiment 10, wherein the pressure in the condensate container is lower than in the heat exchanger on the heating steam side, thus causing a portion of the heating condensate to be re-evaporated and obtained as low pressure steam.
12. Process according to embodiment 11, wherein the heating steam for the bottoms evaporator (7) is provided using a steam ejector supplied with high pressure or medium pressure steam and the low pressure steam obtained in the condensate container.
13. Process according to any of the preceding embodiments, wherein the side rectification column (2) comprises a column bottom in which a liquid bottoms stream that is passed from this column bottom to the combination column (1) is obtained.
14. Process according to any of the preceding embodiments, wherein the bottoms evaporator (7) is a once-through evaporator.
15. Process according to any of the preceding embodiments, wherein at least one of the or two side evaporator systems (5, 6) comprises or consists of a once-through evaporator.

DETAILED DESCRIPTION OF THE INVENTION

The extractive distillation column system according to the invention is an extractive distillation column system for separation of butenes from a C4-hydrocarbon stream which contains at least butenes and butanes using a solvent, wherein the extractive distillation column system comprises a combination column (1) and a side rectification column (2), wherein the combination column (1) viewed from top to bottom comprises at least the following different sections: a top section in which a stream enriched in butanes compared to the employed C4-hydrocarbon stream is obtained: a random packing section which comprises at least two random packing beds: a collection section which comprises at least two liquid collectors, preferably chimney trays; a regeneration section which comprises at least one random packing bed: and a bottom section in which the solvent is obtained: and wherein arranged on the combination column (1) are at least two side evaporator systems (5, 6) in which in each case a liquid phase from one of the liquid collectors of the collection section is at least partially evaporated and subsequently recycled via a respective inlet (5a, 6a) to the collection section, wherein the inlet (5a) is arranged spatially at least one liquid collector above the inlet (Sa);

wherein the side rectification column (2) comprises at least two separating trays or at least one random packing or structured packing bed and is supplied with a gaseous phase which is obtained from the collection section of the combination column (1) below the inlet (5a) but above or at the same height as the inlet (6a). In a preferred embodiment of the present invention the top section comprises trays or random packings.

It is noted that the respective liquid phase that is withdrawn from one of the liquid collectors of the collection section and passed through the side evaporator systems (5, 6) is predominantly in liquid form. However, since the combination column also comprises gaseous phases it may be the case that portions of the gaseous phase are entrained with the liquid phase, for example in the form of gas bubbles, albeit to a (very) small extent. The term "liquid phase" shall explicitly not exclude this possibility.

According to the invention the present combination column (1) comprising the respective sections constitutes a combination of an absorber and a portion of the desorber of known extractive distillation columns. The spatially upper portion of the combination column, i.e. the top section, the random packing section and a portion of the collection section, are comparable with the absorber where the butenes from the C4-hydrocarbon stream are transferred to the solvent. The spatially lower portion of the combination column, i.e. a portion of the collection section, the regeneration section and the bottom section, are comparable with a portion of the desorber (spatially the lower portion of a desorber) where the butenes are removed from the solvent. The side rectification column (2) is comparable with the spatially upper portion of a desorber since the butenes separated from the solvent are obtained overhead there. The side rectification column (2) may be configured as a dedicated column (cf. FIGS. 1 and 2) or integrated into the combination column (1) (cf. FIGS. 3 and 4), i.e. may be arranged in a common column shell with the combination column (1).

The advantages of the extractive distillation column system according to the invention are readily apparent. In both embodiments no pump is required between the combination column (1) and the side rectification column (2). The costs incurred for acquisition and operation are avoided. A side rectification column (2) according to the invention may further be much smaller than the second column (desorber) of known plants. The column system according to the invention thus also requires less space. If the side rectification column (1) is integrated into the combination column (1) even less space is required. In addition, no pipe conduits to the side rectification column (2) are necessary.

The present invention relates to the separation of butenes from C4-hydrocarbon streams using the extractive distillation column system according to the invention. C4-hydrocarbon streams typically also contain alkanes (n-butane, isobutane) in addition to the butenes. In the context of the present invention—unless something else is being described—the term butanes is to be understood as meaning both n-butane and isobutane. The process according to the invention may therefore employ all C4-hydrocarbon streams which contain at least butenes and butanes provided that the amounts in which the butenes and/or butanes are present allow economic performance of the process. In a preferred embodiment of the present invention the employed C4-hydrocarbon stream consists essentially, i.e. to an extent of more than 98% by weight, preferably to an extent of more than 99% by weight, of butanes and butenes. The corresponding streams may also comprise small amounts of impurities or other hydrocarbons, such as 1,3-butadiene, C3- or C5-hydrocarbons.

The solvent employed is a liquid solvent which dissolves primarily the butenes of the employed gaseous C4-hydrocarbon stream. Suitable solvents are aprotic solvents, for example N-methyl-2-pyrrolidone (NMP). It is preferable to employ NMP as solvent. In a further preferred embodiment of the present invention the solvent contains water, in particular in the range from 1% to 10% by weight, preferably from 4% to 9% by weight, in each case based on the total amount of solvent. The combination column (1) of the extractive distillation column system according to the invention especially comprises a suitable inlet for the solvent which is preferably arranged above the first random packing bed of the random packing section or above the second random packing bed of the random packing section.

The combination column (1) of the extractive distillation column system according to the invention especially also comprises a suitable inlet for the C4-hydrocarbon stream from which the butenes are to be separated. The liquid solvent is introduced to the combination column (1) spatially above the inlet for the C4-hydrocarbon stream, i.e. the inlet for the solvent is above the inlet for the C4-hydrocarbon stream. In a preferred embodiment the inlet for the C4-hydrocarbon stream is arranged at least 1 random packing bed below the inlet for the solvent when viewed from above. In the combination column the liquid solvent trickles downwards and is brought into contact with the (ascending) vaporous C4-hydrocarbon stream to transfer a portion of the C4-hydrocarbon stream containing predominantly butenes to the solvent.

Before the C4-hydrocarbon stream passes into the combination column (1) via the inlet the stream is preferably at least partially evaporated. To this end the extractive column system may comprise a feed evaporator (4) which at least partially evaporates the C4-hydrocarbon stream upstream of the inlet into the combination column (1). It is advantageous that the evaporation need not be effected entirely in the combination column (1).

The extractive distillation column system according to the invention comprises two side evaporator systems (5, 6). The two side evaporator systems (5, 6) are arranged one below the other, wherein the streams at least partially evaporated therein are each recycled to the collection section of the combination column (1) via an inlet (5a, 6a). Inlet (5a) belongs to the side evaporator system (5) and inlet (6a) belongs to the side evaporator system (6). The side evaporator system (5) according to the invention preferably comprises a single evaporator or two evaporators arranged in parallel or sequentially. If the side evaporator system (5) comprises two evaporators arranged in parallel or sequentially an additional inlet into the collection section of the combination column (1) may be present. This additional inlet would be spatially above or at the same height as the inlet (5a). The side evaporator system (6) according to the invention preferably comprises a single evaporator or two evaporators arranged in parallel or sequentially. If the side evaporator system (6) comprises two evaporators arranged in parallel or sequentially an additional inlet into the collection section of the combination column (1) may be present. This additional inlet would be spatially below or at the same height as the inlet (6a).

Should the side evaporator system (5) and/or the side evaporator system (6) comprise two evaporators arranged in parallel or sequentially it may be necessary for the collection section of the combination column (1) to comprise more than two liquid collectors to which the recycled streams from the respective evaporator are supplied and/or from which they are withdrawn.

Preferably arranged at the bottom section of the combination column (1) of the extractive distillation column system is a bottoms evaporator (7) which at least partially evaporates the liquid obtained in the column bottom to outgas any residual butenes from the solvent. Regenerated, i.e. depleted in the butenes, hot solvent is then obtained in the column bottom. The solvent obtained in the column bottom is preferably recycled to the inlet for the solvent. In a preferred embodiment the heat of the solvent recycled to the inlet of the combination column (1) is used for heat integration, i.e. the heat of the solvent is preferably used for evaporation in the feed evaporator (4) and for evaporation in the side evaporator systems (5, 6). The feed evaporator (4) and the side evaporator systems (5, 6) are preferably fitted with a heat exchanger which allows this heat transfer.

The heat integration removes heat from the solvent. The reason for this is not only that other streams or columns are thus to be heated but rather primarily the cooling of the solvent. If in the course of the heat integration sufficient heat is withdrawn from the solvent, i.e. it has a suitable temperature, the solvent may be passed directly into the random packing section of the combination column (1). However, it is also conceivable that despite the heat integration present the solvent does not yet have the correct temperature. In such a case the solvent may be passed through a residual cooler after the heat integration and before entry into the combination column (1), in order to be cooled to a suitable temperature.

Heat is a process parameter. The heat supplied or removed corresponds to the change in internal energy minus the work done. The terms heat, heat transport and heat integration used in the present invention are always based on this definition.

The configuration of the side rectification column (2) is characterized by at least two separating trays or by a random packing or structured packing bed. The side rectification column is supplied with a gaseous phase which is withdrawn from the collection section of the combination column (1) below the inlet (5a) but above or at the same height as the inlet (6a). The gaseous phase especially comprises predominantly butenes but may also comprise inter alia residual solvents, for example in the form of entrained droplets. It is preferable according to the invention when the solvent residues are separated and recycled to the combination column, for example through a suitable conduit. The inlet for the recycled solvent residues is accordingly in the collection section of the combination column (1). A stream enriched in butenes relative to the employed C4-hydrocarbon stream can then be withdrawn at the top of the side rectification column (2).

The present invention further provides a process for separation of butenes from C4-hydrocarbon streams by extractive distillation using the extractive distillation column system according to the invention which is described hereinabove. The separation of the butenes is effected at least by the following steps:

supplying a C4-hydrocarbon stream at least partially evaporated in a feed evaporator (4) to the random packing section of the combination column (1) and supplying the liquid solvent at least one random packing bed above the C4-hydrocarbon stream, with the result that the C4-hydrocarbon stream and the solvent are brought into contact with one another and predominantly butenes are transferred from the C4-hydrocarbon stream to the solvent to obtain a laden solvent;

wherein the laden solvent is collected in a liquid collector of the collection section, passed through a first side evaporator system (5), at least partially evaporated therein and then recycled to the collection section via the inlet (5a):

wherein a liquid phase obtained in a further liquid collector of the collection section is passed through the second side evaporator system (6), at least partially evaporated therein and then via the inlet (6a) recycled to the collection section, from where the liquid phase passes into the regeneration section:

wherein the liquid phase obtained below the last random packing bed of the regeneration section and containing the solvent and residual butenes and/or butanes is passed through a bottoms evaporator (7) and then passed into the bottom section, with the result that any butenes and/or butanes present in the solvent are at least partially outgassed and the resulting solvent is withdrawn as a bottoms stream and recycled to the random packing section; and providing a gaseous stream containing at least butenes and residual solvent below the inlet (5a) but above or at the same height as the inlet (6a) from the collection section and supplying this gaseous stream to the side rectification column (2), with the result that a stream enriched in butenes is obtained at the top of the side rectification column, characterized in that the heat of the solvent withdrawn as the bottoms stream is at least partially used for heat integration where heat of the solvent is transferred in the first side evaporator system (5), in the second side evaporator system (6) and in the feed evaporator (4).

The present process relates to the separation of butenes from butene-containing C4-hydrocarbon streams. These streams typically also contain alkanes (n-butane, isobutane) in addition to the butenes. In the context of the present invention—unless something else is being described—the term butanes is to be understood as meaning both n-butane and isobutane. The process according to the invention may therefore employ all C4-hydrocarbon streams which contain at least butenes and butanes provided that the amounts in which the butenes and/or butanes are present allow economic performance of the process. In a preferred embodiment of the present invention the employed C4-hydrocarbon stream consists essentially, i.e. to an extent of more than 98% by weight, preferably to an extent of more than 99% by weight, of butanes and butenes. The corresponding streams may also contain impurities or other hydrocarbons, such as 1,3-butadiene or C5-hydrocarbons, in small amounts.

The solvent employed is a liquid solvent which dissolves primarily the butenes of the employed gaseous C4-hydrocarbon stream. Suitable solvents are aprotic solvents, for example N-methyl-2-pyrrolidone (NMP). It is preferable to employ NMP as solvent. In a further preferred embodiment of the present invention the solvent contains water, in particular in the range from 1% to 10% by weight, preferably from 4% to 9% by weight, in each case based on the total amount of solvent.

The liquid solvent is supplied to the combination column (1) spatially above the inlet for the C4-hydrocarbon stream. In the combination column (1) the liquid solvent trickles downwards and is brought into contact with the (ascending) vaporous C4-hydrocarbon stream to transfer a portion of the C4-hydrocarbon stream containing predominantly butenes to the solvent to form a laden solvent. The C4-hydrocarbon stream and the solvent are brought into contact with one another in particular in countercurrent. In a preferred embodiment of the present invention the portion of the C4-hydrocarbon stream transferred to the solvent comprises at least 70% by weight, particularly preferably at least 80% by weight, of butenes, based on the composition of the portion of the C4-hydrocarbon stream transferred to the solvent. This has the result that in particular at least 80%, particularly preferably at least 90%, of the butenes present in the employed C4-hydrocarbon stream are transferred to the solvent.

The laden solvent flows downwards in the combination column (1) and is collected in a suitable liquid collector of the collection section, in particular a chimney tray. The laden solvent is withdrawn from the liquid collector, passed through the first side evaporator system (5) and then recycled into the collection section via the inlet (5a) below the liquid collector. The side evaporator system (5) according to the invention preferably comprises or preferably consists of a once-through evaporator where the laden solvent is passed through the evaporator only once. This allows achievement of the lowest possible temperatures, thus making it possible to prevent fouling. The side evaporator system (5) according to the invention also preferably comprises a single evaporator or two evaporators arranged in parallel or sequentially. If the side evaporator system (5) comprises two evaporators arranged in parallel or sequentially an additional inlet into the collection section of the combination column (1) may be present. This additional inlet would be spatially above or at the same height as the inlet (5a).

In a further liquid collector of the collection section a liquid phase is obtained, withdrawn there, passed through the second side evaporator system (6) and then recycled into the collection section via the inlet (6a) below this liquid collector. The remaining (unevaporated) liquid phase passes from there into the regeneration section. The side evaporator system (6) according to the invention preferably comprises or preferably consists of a once-through evaporator where the liquid phase is passed through the evaporator only once. This allows achievement of the lowest possible temperatures, thus making it possible to prevent fouling. The side evaporator system (6) according to the invention preferably also comprises a single evaporator or two evaporators arranged in parallel or sequentially. If the side evaporator system (6) comprises two evaporators arranged in parallel or sequentially an additional inlet into the collection section of the combination column (1) may be present. This additional inlet would be spatially below or at the same height as the inlet (6a).

The liquid collectors from which the laden solvent or the liquid phase is withdrawn and passed to the side evaporator systems (5, 6) are thus spatially arranged one below the other, wherein the liquid collector through which the laden solvent passes to the side evaporator system (5) is arranged above the liquid collector through which the liquid phase passes to the side evaporator system (6). The streams at least partially evaporated in the side evaporator systems (5, 6) are each recycled to the collection section of the combination column (1) via an inlet (5a, 6a). The gaseous portion of these respectively recycled streams ascends to the top while the liquid portion of these streams passes further downwards in the combination column.

The liquid phase flows further downwards from the collection section via the regeneration section comprising at least one random packing bed. Below the last random packing bed of the regeneration section the liquid phase is preferably collected in a suitable collector. The liquid phase arriving below the last random packing bed or optionally collected in the collector and containing the solvent and residual butenes and/or butanes is passed through a bottoms evaporator (7) and then passed into the bottom section, with the result that any butenes and/or butanes present in the solvent are at least partially outgassed. The bottom of the combination column (1) is at an elevated temperature. The temperature in the bottom of the combination column (1) is preferably between 120° C. and 200° C., more preferably between 130° C. and 195° C.

The bottoms evaporator (7) is preferably a once-through evaporator where the liquid phase is passed through the evaporator only once. This allows achievement of the lowest possible temperatures, thus making it possible to prevent fouling. Smaller average temperature differences are also made possible, thus allowing the heat transfer to be simplified. The bottoms evaporator (7) may also be configured as a multi-stage apparatus, i.e. a plurality of heat exchangers or a plurality of evaporators belonging to the bottoms evaporator (7) may be present. The solvent is then obtained in the bottom section of the combination column and recycled to the random packing section of the combination column (1), in particular to the corresponding inlet.

An important feature of the present invention is the heat integration using the heat of the solvent on the way from the column bottom to the random packing section of the combination column (1) and optionally of the hot condensate obtained in the bottoms evaporator (7). According to the invention the heat of the solvent, preferably of the NMP, withdrawn in the bottom of the combination column (1) is used for heat integration where heat of the solvent is transferred in the first side evaporator system (5), in the second side evaporator system (6) and in the feed evaporator (4).

The heat for evaporation in the bottoms evaporator (7) may be introduced in a heat exchanger by heat transfer from a suitable heat transfer medium. The heat transfer medium may be in particular heating steam employed in the form of medium pressure or high pressure steam. A preferred heating steam is a medium pressure steam having a temperature of 150° C. to 270° C., preferably of 160° C. to 250° C. The medium pressure steam preferably has a pressure of 15 to 30 bar absolute, particularly preferably of 17 to 25 bar absolute. Also employable as heating steam is a steam having a pressure of >30 bar absolute. Such a heating steam may also be referred to as high pressure steam.

The heating steam used for evaporation in the bottoms evaporator (7) may undergo at least partial condensation in the heat exchanger, thus generating a hot condensate at a pressure of 10 to 20 bar absolute, preferably 12 to 17 bar absolute, and a temperature of 150° C. to 210° C., preferably 160° C. to 200° C. Preferably arranged downstream of the heat exchanger is a condensate container in which the hot condensate may be separated from the steam. The pressure in the condensate container is preferably lower than in the heat exchanger on the heating steam side. The low pressure may result in a portion of the hot condensate evaporating, as a result of which the combined steam, i.e. the uncondensed proportion of the heating steam and the hot condensate evaporated in the condensate container by decompression, is obtained as low pressure steam in the condensate container. In the present case low pressure steam preferably has a pressure of more than 0 bar and less than 10 bar absolute. The temperature of the low pressure steam is preferably 100° C. to 180° C.

The low pressure steam obtained there still contains energy which may be exploited. However, this is not advantageous from an energetic or economic standpoint. This energy can, however, be utilized in a preferred embodiment of the present invention. To this end, the heating steam used for evaporation in bottoms evaporator (7) may be provided using a, preferably controllable, steam ejector (thermocompressor). The thermocompressor is then supplied both with the employed heating steam, originating from an appropriate steam network for example, here especially the preferably employed medium pressure steam, and also with the low pressure steam from the condensate container, thus forming a mixed steam which is accordingly the heat transfer medium for the bottoms evaporator (7). In this embodiment the mixed steam is accordingly the heating steam. Such a steam ejector is configured such that it is operated with a motive steam and by means of a negative pressure (back pressure in the steam ejector) can aspirate suction steam from a container to then form the mixed steam employed as the heat transfer medium. The motive steam is in the present case the heating steam or the medium pressure steam, with which the low pressure steam is aspirated from the condensate container as suction steam and mixed with the motive steam.

The advantage of such an embodiment is obvious. The energy of the low pressure steam obtained in the condensate container may be utilized, thus saving energy and costs. Such a procedure can also be advantageous for another reason. The employed steam ejector may be controllable such that the amounts of medium pressure/high pressure and low pressure steam can be adjusted, for example according to particular process parameters. The amount of suction steam is adjusted via the amount of motive steam. The amounts of low pressure and medium pressure steam may be adjusted for example according to the temperature in the combination column (1).

A stream enriched in butanes compared to the employed C4-hydrocarbon stream is then especially obtained at the top of the combination column (1). The overhead pressure in the combination column (1) may be between 1 and 7 bar absolute, preferably between 2 and 6.5 bar absolute. The stream enriched in butanes may additionally contain water originating from the solvent. This water may be separated in a subsequent step. The stream enriched in butanes is withdrawn at the top of the combination column and subjected to a single- or multi-stage condensation to condense out a water-containing stream and a butane-containing product stream. These two streams may be separated from one another in a suitable apparatus, for example a spider. The water-containing stream separated from the butane-containing product stream may be passed to the combination column (1) or to the side rectification column (2) and/or partially discharged from the process depending on its composition.

The butane-containing product stream thus obtained from the condensation may still contain small amounts of water, in particular in an amount of up to 1500 ppmw, based on the total composition of the butane-containing product stream. In addition, the butane-containing product stream obtained from the condensation may further contain residual butenes, wherein the streams contain typically less than 20% by weight, preferably less than 15% by weight, particularly preferably less than 5% by weight, of butenes, based on the total composition of the butane-containing product stream.

Depending on the requirements for the obtained butane-containing product stream it may be necessary for the butane-containing product stream to be subjected after the condensation to a drying, preferably in a drying column, to separate the water still present. The butane-containing product stream preferably contains a maximum amount of water of 50 ppmw, preferably of 25 ppmw, after the drying. The water obtained in the drying or the vapour stream from the drying may be recycled for condensation in the combination column (1).

A gaseous stream is obtained at the collection section of the combination column (1) below the inlet (5a) but above or at the same height as the inlet (6a) and supplied to the side rectification column. The gaseous phase contains predominantly butenes but may also still contain inter alia residues of butanes and solvent, for example in the form of droplets. This side rectification column (2) comprises, as already mentioned, at least two separating trays or at least one random packing or structured packing bed which are used in particular for separation of solvent. The overhead pressure in the side rectification column may be between 1 and 7 bar absolute, preferably between 2 and 6.5 bar absolute. The pressure in the combination column (1) and the side rectification column (2) is preferably coupled.

A stream enriched in butenes compared to the employed C4-hydrocarbon stream is then especially obtained at the top of the side rectification column (2). This stream enriched in butenes may additionally contain water originating from the solvent. This water may be separated in a subsequent step. The stream enriched in butenes is withdrawn at the top of the side rectification column (2) and subjected to a single- or multi-stage condensation to condense out a water-containing stream, which may contain not only water but also residues of organics, as well as a butene-containing product stream. These two streams may be separated from one another in a suitable apparatus, for example a spider. The water-containing stream separated from the butene-containing product stream may then be recycled to the side rectification column (2) or to the combination column. Discharging the entirety of or a portion of the water-containing stream to keep back the organics present therein is also possible.

In a preferred embodiment of the present invention the condensation of the stream enriched in butenes withdrawn at the top of the side rectification column (2) is configured as a two-stage condensation, wherein in a first stage a water-containing stream is condensed out and then recycled to the side rectification column (2) and in the second stage the butene-containing product stream is condensed out. However, it may also be the case that any water present is also condensed out in the second stage. This residual water may be separated from the butene-containing product stream via a suitable apparatus, for example a spider.

The butene-containing product stream obtained from the condensation preferably contains less than 20% by weight, more preferably less than 16% by weight, of butanes based on the total composition of the butene-containing product stream. By contrast, the butene-containing product stream obtained from the condensation preferably has a butene content of at least 70% by weight, more preferably of at least 75% by weight, particularly preferably of at least 86% by weight, based on the total composition of the butene-containing product stream.

A liquid bottoms stream which contains substantially solvent introduced from the combination column (1) can be obtained in the lower portion of the side rectification column (2) or in the bottom of the side rectification column (2). This stream is only obtained in the embodiment where the side rectification column (2) is configured as a dedicated column (cf. FIGS. 1 and 2). This liquid bottoms stream may be (re)cycled from the side rectification column (2) to the combination column (1). The recycled stream is introduced to the combination column (1) at a suitable point, for example where it is advantageous in terms of concentration.

Figure 1:
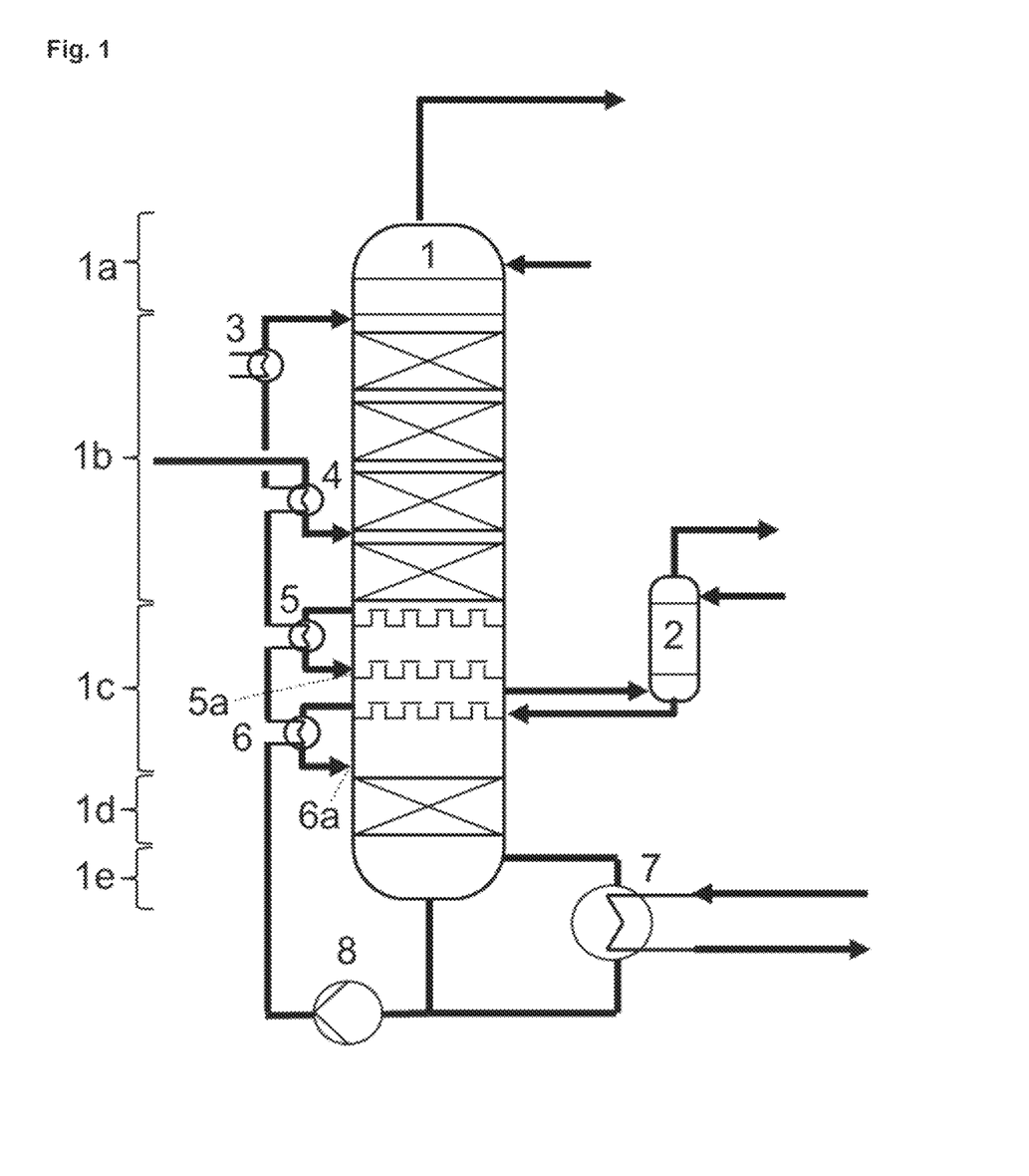
FIG. 1 shows a basic configuration of the present invention.

The present invention is hereinbelow elucidated with reference to figures. The figures are for illustration but are not to be understood as limiting, FIG. 1 shows the basic configuration of the present invention. The liquid C4-hydrocarbon stream is evaporated via a feed evaporator (4) and passed into the random packing section (1b) of the combination column (1). The solvent is—when necessary—brought to the desired temperature via a residual cooler (3) and likewise passed into the random packing section (1b) of the combination column (1), wherein the inlet is spatially above the inlet for the C4-hydrocarbon stream, in the present case above the first random packing bed. The stream enriched in butanes, which is withdrawn, is obtained at the top section (1a) of the combination column (1). A possible condensation is not shown here, merely the recycling of a possible substream is indicated by the arrow. The laden solvent is collected in a liquid collector in the collection section (1c) of the combination column (1) as indicated by the chimney tray in the figure. At least a portion of the laden solvent is withdrawn there and recycled to the collection section (1c) via the first side evaporator system (5) and subsequently via the inlet (5a). A liquid phase is collected in a further liquid collector, withdrawn therefrom and via the second side evaporator system (6) via the inlet (6a) recycled to the collection section, from where the liquid phase passes into the regeneration section (1d). Below the last random packing bed the liquid phase obtained there is withdrawn and passed via the bottoms evaporator (7) to the bottom (1e) of the combination column (1). The solvent depleted in butenes is then withdrawn from the bottom (1e) of the combination column (1) and using a pump (8) recycled to the random packing section of the combination column (1) via the side rectification systems (5, 6) and the feed evaporator. Between the inlet (5a) and the inlet (6a) a gaseous stream is withdrawn and passed to the side rectification column (2) where residual solvent and water are to be separated from the butenes. The stream enriched in butenes is obtained at the top of the side rectification column (2). This stream may be subjected to a single- or multi-stage condensation which is not shown in the figure. Only a possible recycle stream is indicated by the arrow. Obtained here in the bottom of the side rectification column (2) is a liquid phase which may be recycled to the collection section of the combination column (1).

Figure 2:
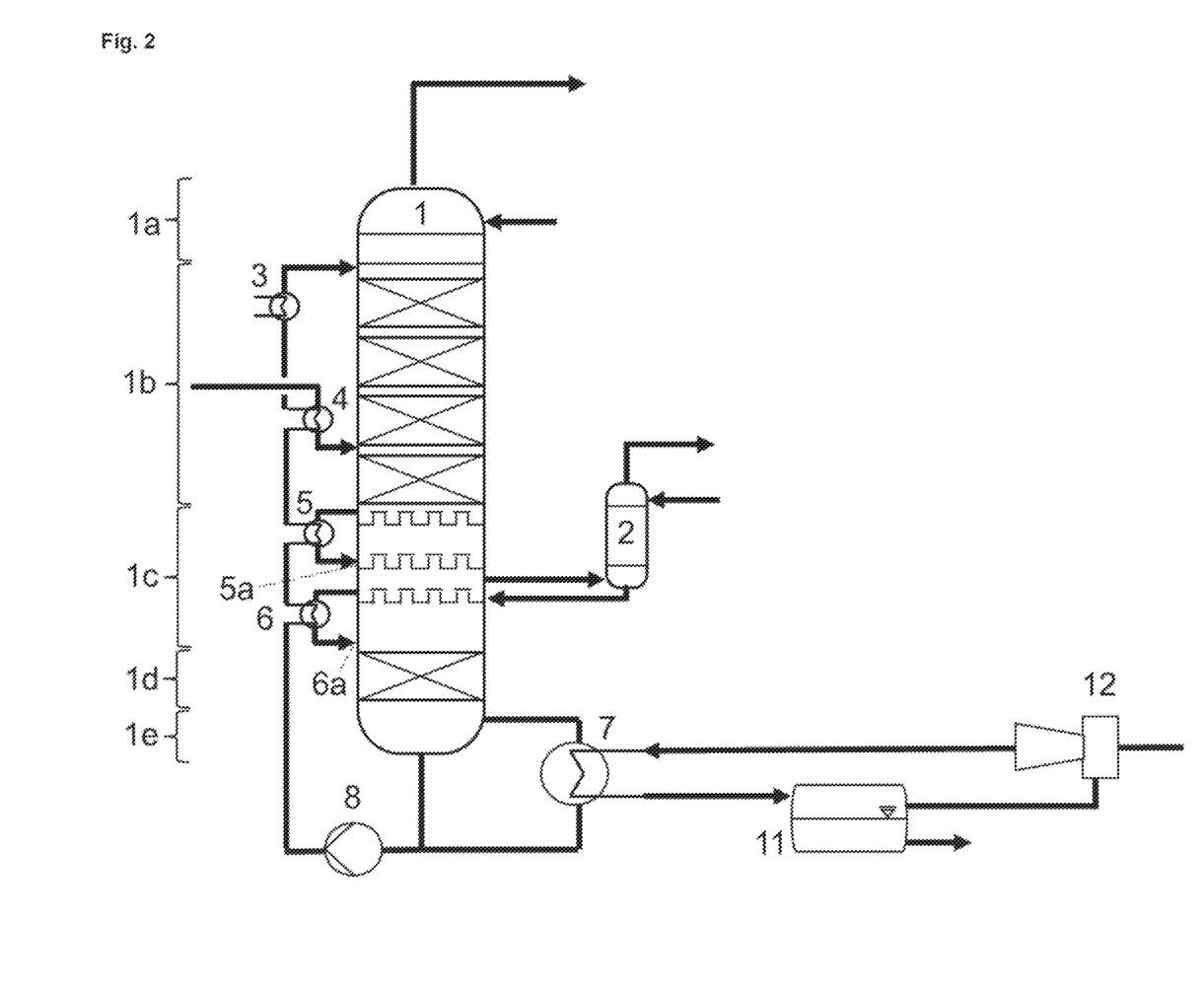
FIG. 2 shows a further preferred embodiment of the present invention where a steam ejector is present at the bottoms evaporator.

FIG. 2 shows a further preferred embodiment of the present invention where a steam ejector (12) is present at the bottoms evaporator (7). This steam ejector is supplied with the regular heating steam, i.e. for example the medium pressure steam from the steam network, and the low pressure steam obtained in the condensate container (11), thus forming a mixed steam which is then used as heating steam for the bottoms evaporator (7). The mode of operation of a steam ejector is elucidated in the description of FIG. 3. Everything else corresponds to what has been previously specified in connection with FIG. 1.

Figure 3:
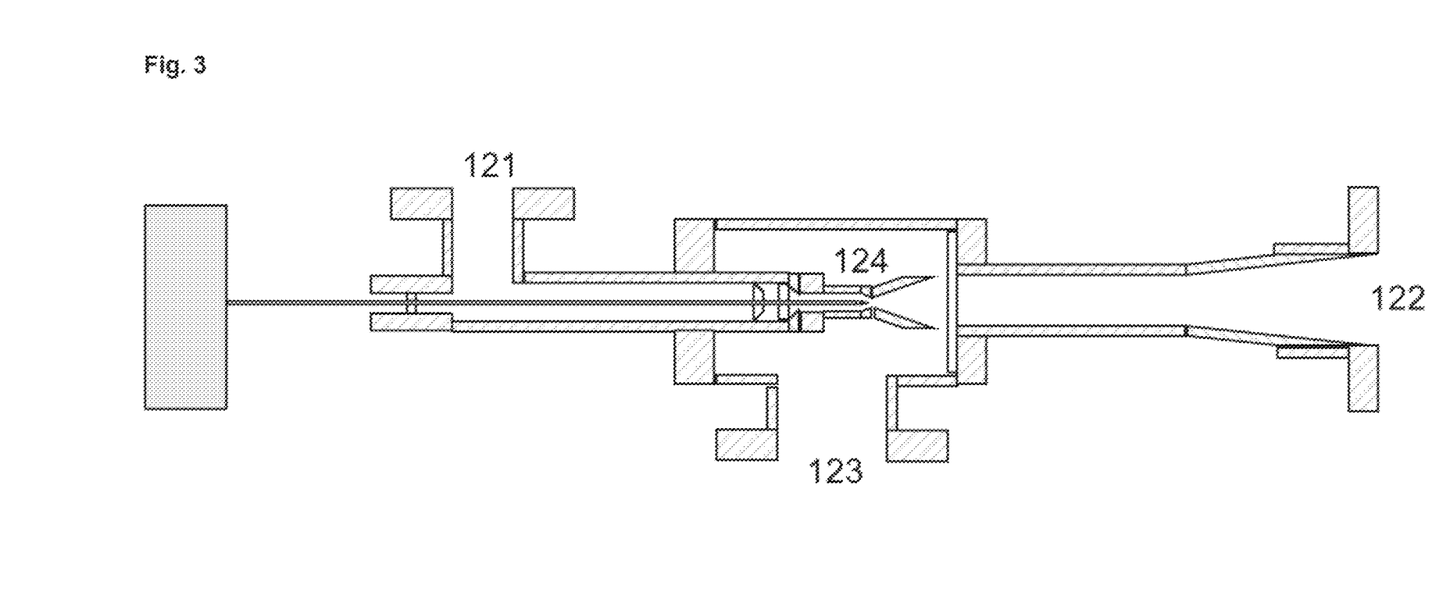
FIG. 3 shows the schematic construction of a steam ejector.

FIG. 3 shows the schematic construction of a steam ejector (12). Here, the motive steam (121) is the heating steam, in particular the medium pressure steam from the steam network. The suction steam (123) is the low pressure steam from the condensate container. The two are mixed via the control unit (124) and passed via the exit to the bottoms evaporator (7) as mixed steam (122). The amounts of motive steam and suction steam can be adjusted via the control unit, thus making it possible to influence the pressure and temperature of the mixed steam and thus the possible heating output.

Figure 4:
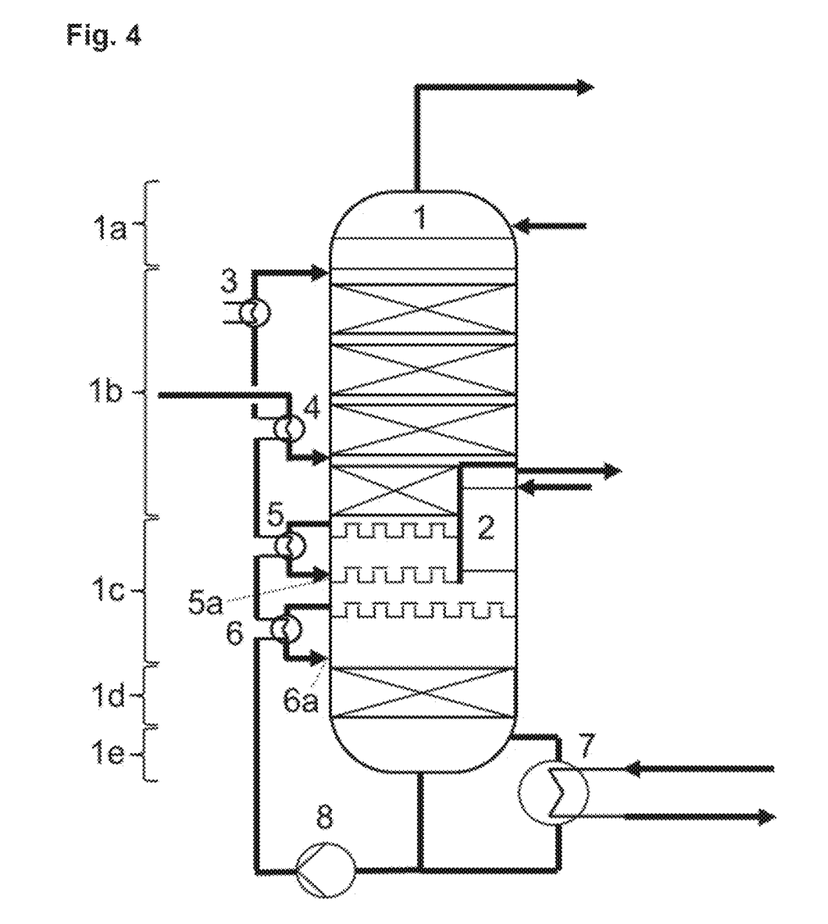
FIG. 4 shows a further subject of the present invention.

FIG. 4 shows a further subject of the present invention. The mode of operation corresponds to the process shown in FIG. 1 and differs only in its construction. Accordingly the combination column (1) and the side rectification column (2) are distinct units having the functions described according to the invention. However, the side rectification column has been spatially integrated into the combination column, i.e. is constructionally implemented in a single column shell. The side rectification column (2) is open in the spatially downward direction and is supplied with an ascending gaseous phase which contains at least butenes and residual solvent and water. The stream enriched in butenes is obtained at the side rectification column (2). This stream may be subjected to a single- or multi-stage condensation which is not shown in the figure. Only a possible recycle stream is indicated by the arrow.

Figure 5:
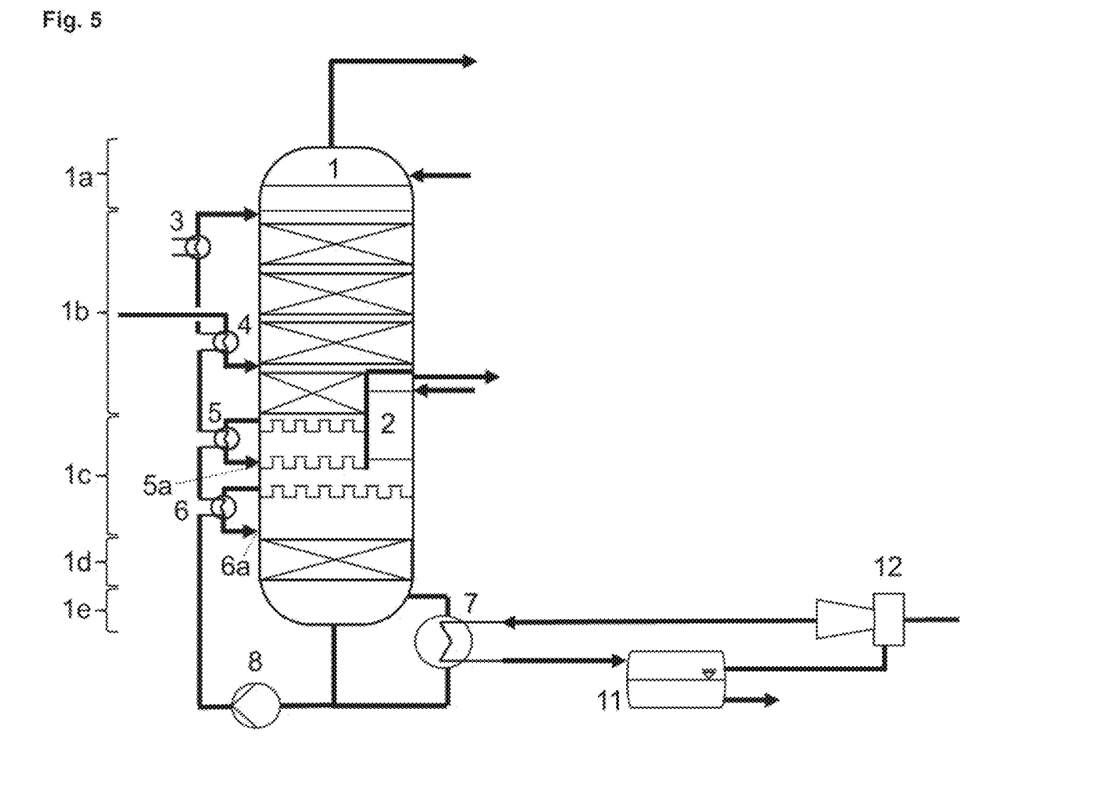
FIG. 5 shows a further preferred embodiment of the present invention where a steam ejector is present at the bottoms evaporator.

FIG. 5 shows a further preferred embodiment of the present invention where a steam ejector (12) is present at the bottoms evaporator (7). This steam ejector is supplied with the regular heating steam, i.e. for example the medium pressure steam from the steam network, and the low pressure steam obtained in the condensate container (11), thus forming a mixed steam which is then used as heating steam for the bottoms evaporator (7). The mode of operation of a steam ejector is elucidated in the description of FIG. 3. Everything else corresponds to what has been previously specified in connection with FIG. 1.

The invention claimed is:

1. An extractive distillation column system for separation of butenes from a C4-hydrocarbon stream which contains at least butenes and butanes using a solvent, wherein the extractive distillation column system comprises:
   a combination column, and
   a side rectification column,
   wherein the combination column from top to bottom comprises at least the following different sections:
      a top section in which a stream enriched in butanes compared to the C4-hydrocarbon stream is obtained;
      a random packing section which comprises at least two random packing beds;
      a collection section which comprises at least two liquid collectors;
      a regeneration section which comprises at least one further random packing bed; and
      a bottom section in which the solvent is obtained;
   wherein arranged on the combination column are at least two side evaporator systems, wherein in each evaporator system a liquid phase from one of the at least two liquid collectors of the collection section is at least partially evaporated and subsequently recycled via a respective first inlet or second inlet to the collection section, wherein the first inlet is arranged spatially at least one liquid collector above the second inlet; and
   wherein the side rectification column comprises at least two separating trays or at least one random packing or structured packing bed and is supplied with a gaseous phase which is obtained from the collection section of the combination column at a location below the first inlet but above or at a same height as the second inlet.

2. The extractive distillation column system according to claim 1, wherein the extractive distillation column system further comprises a feed evaporator which at least partially evaporates the C4-hydrocarbon stream before being passed into the combination column.

3. The extractive distillation column system according to claim 2, wherein the solvent obtained in the bottom section of the combination column is recycled to a third inlet for the solvent.

4. The extractive distillation column system according to claim 3, wherein the solvent is used for heat integration, wherein heat of the solvent is transferred in a first side evaporator system and a second side evaporator system of the at least two side evaporator systems, and in the feed evaporator.

5. The extractive distillation column system according to claim 1, wherein arranged at the bottom section of the combination column is a bottoms evaporator which at least partially evaporates liquid obtained in the bottom section to outgas any residues of butenes from the solvent.

6. The extractive distillation column system according to claim 1, wherein a stream enriched in butenes is withdrawn at a top of the side rectification column.

7. A process for separation of butenes from a C4-hydrocarbon stream containing at least butenes and butanes by extractive distillation in the extractive distillation column system according to claim 1, the process comprising:
   supplying the C4-hydrocarbon stream to a feed evaporator and at least partially evaporating the C4-hydrocarbon stream, and supplying the C4-hydrocarbon stream to the random packing section of the combination column, and supplying the solvent to the combination column at a position at least one random packing bed above the C4-hydrocarbon stream, wherein the C4-hydrocarbon stream and the solvent are brought into contact with one another and predominantly the butenes are transferred from the C4-hydrocarbon stream to the solvent, to obtain a laden solvent;

collecting the laden solvent in a first liquid collector of the at least two liquid collectors of the collection section, passing the laden solvent through a first side evaporator system of the at least two side evaporator systems, wherein the laden solvent is at least partially evaporated therein, and recycling the laden solvent to the collection section via the first inlet;

passing a first liquid phase obtained in a second liquid collector of the at least two liquid collectors of the collection section through a second side evaporator system of the at least two side evaporator systems, wherein the first liquid phase is at least partially evaporated therein, and recycling the first liquid phase via the second inlet to the collection section, and passing the first recycled liquid phase into the regeneration section;

passing a second liquid phase obtained below a last random packing bed of the at least one further random packing bed of the regeneration section, wherein the second liquid phase contains the solvent and residual butenes and/or butanes, through a bottoms evaporator and then into the bottom section, wherein the residual butenes and/or butanes present in the solvent are at least partially outgassed and a resulting solvent is withdrawn as a bottoms stream and recycled to the random packing section; and providing a gaseous stream containing at least the butenes and residual solvent below the first inlet but above or at the same height as the second inlet from the collection section, and supplying the gaseous stream to the side rectification column, wherein a stream enriched in the butenes is obtained at a top of the side rectification column, wherein heat of the resulting solvent withdrawn as the bottoms stream is at least partially used for heat integration wherein heat of the resulting solvent is transferred in the first side evaporator system, in the second side evaporator system, and in the feed evaporator.

8. The process according to claim 7, wherein the solvent is N-methyl-2-pyrrolidone (NMP).

9. The process according to claim 7, wherein heat for evaporation in the bottoms evaporator is introduced in a heat exchanger by heat transfer with a suitable heat transfer medium.

10. The process according to claim 9, wherein an employed heating steam undergoes at least partial condensation in the heat exchanger, thus generating a hot condensate at a pressure of 10 to 20 bar absolute, and a temperature of 150° C. to 210° C., which is passed to a condensate container.

11. The process according to claim 10, wherein a pressure in the condensate container is lower than the pressure in the heat exchanger on a heating steam side, thus causing a portion of the hot condensate to be re-evaporated and obtained as low pressure steam.

12. The process according to claim 11, wherein the heating steam for the bottoms evaporator is provided using a steam ejector supplied with high pressure or medium pressure steam and the low pressure steam obtained in the condensate container.

13. The process according to claim 7, wherein the side rectification column comprises a column bottom in which a liquid bottoms stream is obtained, which is passed from the column bottom to the combination column.

14. The process according to claim 7, wherein the bottoms evaporator is a once-through evaporator.

15. The process according to claim 7, wherein at least one of the at least two side evaporator systems comprises or consists of a once-through evaporator.

16. The extractive distillation column system according to claim 1, wherein the at least two liquid collectors of the collection section are chimney trays.

17. The process according to claim 9, wherein the heat transfer medium is heating steam.

18. The process according to claim 10, wherein the hot condensate in the heat exchanger is at a pressure of 12 to 17 bar absolute and a temperature of 160° C. to 200° C.

* * * * *